United States Patent
Simitchieva et al.

(10) Patent No.: US 6,384,034 B2
(45) Date of Patent: May 7, 2002

(54) METHOD OF TREATING MIGRAINES AND PHARMACEUTICAL COMPOSITIONS

(75) Inventors: Kremena Simitchieva, Basking Ridge, NJ (US); Scott A. Reines, New Hope, PA (US); Errol McKinney; Eric J. Sandquiest, both of Doylestown, PA (US); Deepak K. Khannna, Furlong, PA (US); Richard Hargreaves, Terlings Park (GB)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/934,823

(22) Filed: Aug. 22, 2001

Related U.S. Application Data

(63) Continuation of application No. 09/429,274, filed on Oct. 29, 1999, now abandoned.
(60) Provisional application No. 60/106,605, filed on Nov. 2, 1998.

(51) Int. Cl.$^7$ .................. A61K 31/50; A61K 31/495; A61K 31/44; A61K 31/42; A61K 31/415
(52) U.S. Cl. .................. 514/252; 514/335; 514/378; 514/406; 514/460
(58) Field of Search ................. 514/460, 406, 514/378, 335, 252

(56) References Cited

U.S. PATENT DOCUMENTS

| | | | |
|---|---|---|---|
| 5,298,520 A | | 3/1994 | Baker et al. |
| 5,451,588 A | | 9/1995 | Baker et al. |
| 5,527,817 A | | 6/1996 | Baker et al. |
| 5,807,571 A | | 9/1998 | List |
| 5,834,502 A | | 11/1998 | Cheng et al. |
| 5,861,419 A | | 1/1999 | Dube et al. |
| 5,872,145 A | | 2/1999 | Plachetka |
| 5,891,885 A | | 4/1999 | Caruso |
| 5,942,503 A | | 8/1999 | Jung et al. |
| 5,981,526 A | | 11/1999 | Hargreaves |
| 5,994,379 A | * | 11/1999 | Bayly et al. |
| 6,077,539 A | | 6/2000 | Plachetka et al. |
| 6,310,099 B1 | * | 10/2001 | Fujimoto et al. |

FOREIGN PATENT DOCUMENTS

| | | |
|---|---|---|
| EP | 1 051 993 | 5/2000 |
| EP | 1 051 994 | 5/2000 |
| EP | 1 051 995 | 5/2000 |
| WO | WO98/06392 | 2/1998 |
| WO | WO98/20870 | 5/1998 |
| WO | WO00/48583 | 2/2000 |

OTHER PUBLICATIONS

Bates et al., "Subcutaneous sumatriptan during the migraine aura . . . ", DatabaseMeline, AN 95022243, abstract, Neurology, 1994, vol.44/9, pp. 1587–1592.*
Rapoport et al., "Oral sumatriptan in preventing headache reccurrence . . . " Database Caplus, AN 1995:760113, abstract, Neurology, 1995, vol. 45/9, pp. 1505–1509.*
Hannington–Kiff., Sumatriptan relieves and prevents peri–operative migraine attacks", Database Medline, AN 93212901, abstract, Anaesthesia, 1993, vol. 48/2, pp. 144–146.*
Leone et al., "A reveiw of the treatment of primary headaches . . . " Database Medline, AN96435897, abstract, Italian J. of neurological Sciences, 1995, vol. 16/9, pp. 577–586.*
Warner, Timothy, D., et al.; Proc. Natl. Acad. Sci. USA, Pharmacology, vol. 96, pp. 7563–7568, 1999.
Barner, A.—Acandianavian J. of Rheumatology, Supp. 102, pp. 29–37, 1996.
Jezdimirovic, et al.—Veterinarski, G., vol. 53/3–4, pp. 135–145, 1999.
Lund, et al.—Osteoarthritis and Cartilage, vol.5/4, pp. 283–288, 1997.
Baumgartner, M.—Dtsch. Apoth.Ztg., vol. 137/25, pp. 2157–2159, 1997.
Van Ryn, et al.—Expert Opin.Invent Drugs, vol. 6/5, pp. 609–614, 1997.
Newman, et al., Neurology, vol. 51, pp. 307–309, 1998.

* cited by examiner

Primary Examiner—William R. A. Jarvis
Assistant Examiner—Vickie Kim
(74) Attorney, Agent, or Firm—Raynard Yuro; Richard C. Billups; David L. Rose

(57) ABSTRACT

A combination of a $5HT_{1B/1D}$ agonist and a COX-2 selective inhibitor is useful in the treatment and or prevention of migraine.

9 Claims, No Drawings

METHOD OF TREATING MIGRAINES AND PHARMACEUTICAL COMPOSITIONS

CROSS REFERENCE TO RELATED APPLICATIONS

This application is a continuation of U.S. Application Ser. No. 09/429,274, filed Oct. 29, 1999, now abandoned, which claims the benefit of U.S. Provisional Application No. 60/106,605, filed Nov. 2, 1998.

BACKGROUND OF THE INVENTION

Migraines are recurrent, often familial, symptom complexes of periodic attacks of vascular headache. Migraines affect approximately 17% of adult women and 6% of adult men (Stewart et al., *Neurology*, 1994, 44 (suppl. 4), 517–523).

It has been known for some time that sumatriptan, which causes constriction of cranial blood vessels, is an effective treatment for migraine (see, for example, Doenicke et al., *Lancet*, 1988, Vol. 1, 1309–11; and Feniuk & Humphrey, *Drug Development Research*, 1992, 26, 235–40). As such, it is the prototypical example of a class of compounds, including rizatriptan, which have recently been classified (Hartig et al., *TIPS*, 1996, 17, 103–105) as $5\text{-HT}_{1B/1D}$ receptor agonists.

Activation of $5\text{-HT}_{1B}$ and/or $5\text{-HT}_{1D}$ receptors leads to (1) selective vasoconstriction of certain cranial extracerebral blood vessel segments; (2) pre-junctional inhibition of the release of proinflammatory neuropeptides from sensory nerve terminals in the meninges; and (3) attenuation of central nociceptive neurotransmission by inhibition of neurotransmitter release within the trigeminal nucleus caudalis. It is believed that one or more of these three mechanisms is involved in the anti-migraine action of $5\text{-HT}_{1B/1D}$ receptor agonists such as rizatriptan.

Cyclooxygenase (COX), also known as prostaglandin H synthase, is an enzyme implicated in the mediation of pain, fever and inflammation. It catalyzes the oxidative conversion of arachidonic acid into prostaglandin $H_2$, a key intermediate in the biosynthetic pathway of prostaglandins, prostacyclins and thromboxanes, which in turn mediate a variety of physiological effects both beneficial and pathological.

Recently it was discovered that two COX isoforms exist: COX-1, expressed constitutively in many tissues, and COX-2, an induced isoform having elevated levels of expression in inflamed tissues. COX-1 is thought to be involved in ongoing "housekeeping" functions, for example, gastric cytoprotection, while COX-2 is implicated in the pathological effects mentioned above.

Current cyclooxygenase inhibitors such as aspirin, ibuprofen and indomethacin, used as non-steroidal anti-inflammatory drugs (NSAIDs), inhibit both COX-1 and COX-2 and have associated side effects, such as gastrotoxicity, which may be manifested as ulcer formation. COX-2 selective inhibitors act as effective NSAIDs without substantial gastrotoxic side effects. For purposes of this disclosure only, a COX-2 selective inhibitor is defined as a COX inhibitor having a selectivity for the COX-2 isoform relative to the COX-1 isoform.

The treatment of migraines by coadministration of a 5HT agonist and a traditional analgesic, including a NSAID has been described in international patent application WO98/06392.

It has now been found that migraines can be more effectively treated and/or controlled by the co-administration of a $5\text{-HT}_{1B/1D}$ receptor agonist in combination with a COX-2 selective inhibitor, than with a $5\text{HT}_{1B/1D}$ agonist alone, and more safely than with a traditional analgesic in combination with a 5HT agonist.

SUMMARY OF THE INVENTION

The present invention relates to a method of treating or preventing migraines in a mammalian patient in need thereof, which comprises administering to said patient an anti-migraine effective amount of a combination of a COX-2 selective inhibitor and a $5\text{-HT}_{1B/1D}$ receptor agonist.

The invention also relates to a pharmaceutical composition comprising a COX-2 selective inhibitor, a $5\text{-HT}_{1B/1D}$ receptor agonist and a pharmaceutically acceptable carrier therefore.

DETAILED DESCRIPTION

One embodiment of the present invention is a method of treating or preventing migraine with an anti-migraine effective amount of combination of a $5\text{HT}_{1B/1D}$ agonist and a COX-2 selective inhibitor.

Another embodiment of the invention is a pharmaceutical composition comprising a combination of a $5\text{HT}_{1B/1D}$ agonist and a COX-2 selective inhibitor and a pharmaceutically acceptable carrier.

In these two embodiments, examples of the $5\text{HT}_{1B/1D}$ agonist can be selected from rizatriptan (EP 0,497,512), sumatriptan (GB 2,162,522), naratriptan (GB 2,208,646), zolmitriptan (WO91/18897), eleptriptan (WO92/06973), and almotriptan (WO94/02460).

The preferred $5\text{HT}_{1B/1D}$ agonist for use in this invention is rizatriptan, which is N,N-dimethyl-2-[5-(1,2,4-triazol-1-ylmethyl)-1H-indol-3-yl]ethylamine, the benzoate salt thereof being particularly preferred.

Examples of COX-2 inhibitors useful in the methods and compositions described herein include Celebrex® (celecoxib), VIOXX®, MK-663 (WO98/03484), compounds disclosed in WO07/14691, meloxicam, RS 57067, valdecoxib (U.S. Pat. No. 5,663,272) and a compound of the structure:

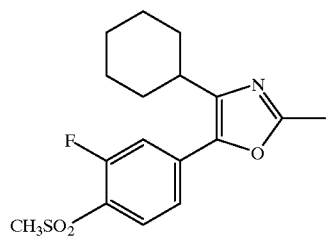

In the novel method of treatment described herein, the two active ingredients can be administered combined in a single dosage form such as described as one embodiment of this invention, or as two separate dosage forms, each containing one of the active ingredients, the two being administered substantially concurrently.

In one aspect of the invention, a method of treating or preventing migraine is disclosed in a mammalian patient in need of such treatment, which comprises administering to the patient a COX-2 selective inhibiting compound and a $5\text{HT}_{1B/1D}$ agonist, or salts or hydrates thereof, in amounts that are effective for treating or preventing migraines.

More particularly, a method is disclosed wherein the $5\text{HT}_{1B/1D}$ agonist is selected from the group consisting of:

sumitriptan, naratriptan, zolmitriptan, eleptriptan, almatriptan and rizatriptan and the COX-2 selective inhibiting compound is selected from the group consisting of: meloxicam, 2-(6-methylpyrid-3-yl)-3-(4-methylsulfonylphenyl)-5-chloropyridine (MK-663), VIOXX® (valdecoxib), RS 57067, Celebrex® (celecoxib), and a compound of structure:

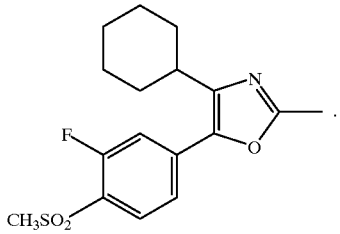

Even more particularly, a methodis disclosed wherein the COX-2 selective inhibitor is VIOXX® and the $5HT_{1B/1D}$ agonist is rizatriptan or a salt or hydrate thereof.

In one aspect, the method is described wherein the $5HT_{1B/1D}$ agonist and COX-2 inhibitor are administered combined in a in single dosage form.

In another aspect, the method is described wherein the $5HT_{1B/1D}$ agonist and COX-2 inhibitor are administered as separate dosage forms substantially concurrently.

In a different aspect, a pharmaceutical composition is included herein which is comprised of a $5HT_{1B/1D}$ agonist and a COX-2 selective inhibiting compound, or salts or hydrates thereof, in combination with a pharmaceutically acceptable carrier.

More particularly, the composition is described wherein the $5HT_{1B/1D}$ agonist is selected from sumitriptan, naratriptan, zolmitriptan, eleptriptan, almatriptan and rizatriptan, and the COX-2 inhibitor is selected from MK-663, VIOXX®, meloxicam, RS57067, celoxib, valdecoxib and a compound of structure:

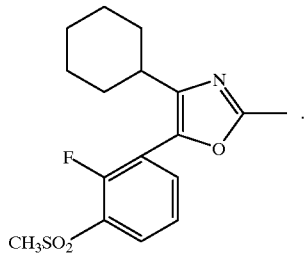

Even more particularly, the composition is described wherein the $5HT_{1B/1D}$ agonist is rizatriptan or a salt thereof, and the COX-2 inhibitor is VIOXX®.

In a preferred combination, a composition is described wherein rizatriptan or a salt thereof, is present in an amount ranging from about 1 to about 10 mg, and VIOXX® is present in an amount ranging from about 10 mg to about 100 mg. More particularly, the rizatriptan is present as the benzoate salt, and VIOXX.

An anti-migraine effective amount of the combination is that amount that will relieve the subject being treated of the symptoms of the migraine attack and the specific dose level and frequency of dosage may vary and will depend upon a variety of factors including the activity of the specific compounds used in combination, the metabolic stability and length of action of the compounds, the age, body weight, general health, sex diet, mode and time of administration, rate of excretion, the severity of the particular condition and the host undergoing therapy. However, dosage levels of the $5HT_{1B/1D}$ on the order of about 0.001 mg/kg to about 250 mg/kg of body weight per day, typically about 0.005 to about 100 mg/kg, more particularly about 0.01 to about 50 mg/kg and especially about 0.05 to about 10 mg/kg per day are useful in the novel method of treatment. Dosage levels of the COX-2 inhibitor of about 0.1 to 500 mg/kg of body weight per day, typically about 0.5 to about 250 mg/kg, more particularly about 5 to about 100 mg/kg and especially about 10 to about 50 mg/kg of body weight per day are useful in the novel method of this invention.

For the treatment of a migraine attack, the active ingredients, separately or in combination, may be administered orally, topically, parenterally, by inhalation, spray, rectally or intravaginally in formulations containing pharmaceutically acceptable carriers.

The term parenteral as used herein includes subcutaneous injections, intravenous, intramuscular, intrasisternal injection or infusion techniques.

The separate active agents or the novel composition of this invention may be in a form suitable for oral use, for example, tablets, troches, lozenges, aqueous or oily suspensions, dispersible powders or granules, emulsions, hard or soft capsules, solutions, syrups and elixirs. Compositions intended for oral use may be prepared according to any method known to the art for the manufacture of pharmaceutical compositions and typically such compositions contain one or more agents selected from the group consisting of sweetening agents, flavouring agents, colouring agents and preservatives in order to provide pharmaceutically elegant and palatable preparations. These excipients may be for example, diluents such as lactose, calcium carbonate, sodium carbonate, calcium phosphate or sodium phosphate; granulating and disintegrating agents, for example, corn starch or alginic acid; binding agents, for example starch, gelatin or acacia, and lubricating agents, for example, magnesium stearate, stearic acid or talc.

The tablets may be uncoated or they may be coated. Coating can be included to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pats. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or miscible solvents such as propylene glycol, PEGs and ethanol, or an oil medium, for example peanut oil, liquid paraffin or olive oil.

Aqueous suspensions contain the active material in admixture with excipients suitable for the manufacture of aqueous suspensions. Such excipients are suspending agents, for example sodium carboxymethylcellulose, methylcellulose, hydroxy-propylmethycellulose, sodium alginate, polyvinyl-pyrrolidone, tragacanth and acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl or n-propyl p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The individual agents or the pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain demulcents, preservatives, flavourants and colouring agents.

The pharmaceutical compositions may be in the form of a sterile injectable aqueous or oleagenous suspension. This suspension may be formulated according to the known art using those suitable dispersing or wetting agents and suspending agents which have been mentioned above.

Injectable compositions are typically in the form of sterile solutions or suspensions, which include the active ingredient in a parenterally-acceptable diluent. Among these are sterile water, dextrose 5% in water (D5W), Ringer's solution and isotonic saline, as well as mixtures thereof. Cosolvents such as ethanol, propylene glycol or polyethylene glycols may also be used. Sterile, injectable oil is occasionally employed as a solvent or suspending medium in intramuscular preparations. A representative example is peanut oil. In addition, fatty acids such as oleic acid, preservatives, buffers and local anesthetics find use in the preparation of intramuscular injectables.

The combination of active ingredients may also be administered rectally or intravaginally as suppositories. These can be prepared by mixing the drug with a suitable non-irritating excipient which is solid at ordinary room temperature but molten at normal or elevated body temperature. Examples of such materials include cocoa butter and polyethylene glycols.

For topical use, creams, ointments, gels, solutions, suspensions and the like containing the compound are employed. (For purposes of this application, topical application includes mouth washes and gargles, as well as transdermal applications.) Topical formulations are comprised of a pharmaceutical carrier, which may include, e.g., cosolvents, emulsifiers, penetration enhancers, preservatives or emollients.

The active ingredients are combined with the carrier to produce the dosage form. For example, a formulation intended for oral administration may contain from as low as about 0.1 mg of the novel combination to as high as about 5 g of combination per dose, compounded with an appropriate and convenient amount of carrier material which may vary from about 5 to about 95 percent of the total composition.

EXAMPLES 1 AND 2

Tablet Preparation

Tablets containing 5 mg and 10 mg of rizatriptan benzoate and 10 mg of Vioxx were prepared as follows:

|  | Example 1 | Example 2 |
| --- | --- | --- |
| Rizatriptan benzoate | 5.0 mg | 10.0 mg |
| Vioxx | 10.0 mg | 10.0 mg |
| Microcrystalline cellulose | 42.0 mg | 39.5 mg |
| Modified food corn starch | 42.0 mg | 39.5 mg |
| Magnesium stearate | 1.0 mg | 1.0 mg |

All of the active ingredients, cellulose, and a portion of the corn starch are mixed and granulated to 10% corn starch paste. The resulting granulation is sieved, dried and blended with the remainder of the corn starch and magnesium stearate. The resulting granulation is then compressed into tablets.

What is claimed is:

1. A method of preventing migraine in a mammalian patient in need of such prevention, which comprises administering to the patient a COX-2 selective inhibiting compound and a $5HT_{1B/1D}$ agonist, or salts or hydrates thereof, in amounts that are effective for preventing migraines, wherein the $5HT_{1B/1D}$ agonist is selected from the group consisting of: naratriptan, zolmitriptan, eletriptan, almotriptan and rizatriptan and the COX-2 selective inhibiting compound is selected from the group consisting of: MK-663, rofecoxib, RS 57067, celecoxib, valdecoxib and a compound of structure:

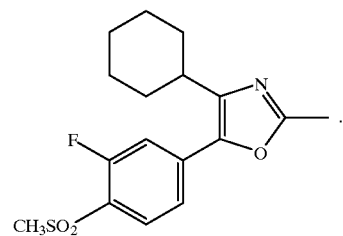

2. The method according to claim 1 wherein the COX-2 selective inhibitor is rofecoxib and the $5HT_{1B/1D}$ agonist is rizatriptan.

3. The method of claim 1 wherein the $5HT_{1B/1D}$ agonist and COX-2 selective inhibiting compound are administered combined in a single dosage form.

4. The method of claim 1 wherein the $5HT_{1B/1D}$ agonist and COX-2 selective inhibiting compound are administered as separate dosage forms substantially concurrently.

5. The method according to claim 1 wherein the COX-2 selective inhibiting compound is rofecoxib.

6. The method according to claim 1 wherein the COX-2 selective inhibiting compound is MK-663.

7. The method according to claim 1 wherein the COX-2 selective inhibiting compound is celecoxib.

8. The method according to claim 1 wherein the COX-2 selective inhibiting compound is valdecoxib.

9. The method according to claim 1 wherein the $5HT_{1B/1D}$ agonist is eletriptan and the COX-2 selective inhibiting compound is selected from the group consisting of: celecoxib and valdecoxib.

* * * * *